United States Patent
Miyazaki

[11] Patent Number: 5,989,185
[45] Date of Patent: Nov. 23, 1999

[54] ENDOSCOPE APPARATUS

[75] Inventor: Atsushi Miyazaki, Hachioji, Japan

[73] Assignee: Olympus Optical Co., Ltd., Tokyo, Japan

[21] Appl. No.: 09/033,698

[22] Filed: Mar. 3, 1998

Related U.S. Application Data

[62] Division of application No. 08/515,578, Aug. 16, 1995.

[30] Foreign Application Priority Data

Nov. 25, 1994 [JP] Japan .................. 6-291602

[51] Int. Cl.$^6$ ................................. A61B 1/05
[52] U.S. Cl. .................. 600/175; 600/173; 600/172; 600/166
[58] Field of Search .................. 600/170, 171, 600/172, 173, 174, 175, 176, 177, 180

[56] References Cited

U.S. PATENT DOCUMENTS

| | | | |
|---|---|---|---|
| 3,818,902 | 6/1974 | Kinoshita | 600/173 |
| 3,889,662 | 6/1975 | Mitsui | 600/173 |
| 3,918,438 | 11/1975 | Hayamizu | 600/173 |
| 4,588,294 | 5/1986 | Siegmund | 600/173 |
| 4,697,577 | 10/1987 | Forkner | 600/173 |
| 4,699,463 | 10/1987 | D'Amelio | 600/173 |
| 4,706,653 | 11/1987 | Yamamoto . | |
| 4,838,247 | 6/1989 | Forkner | 600/173 |
| 4,846,154 | 7/1989 | Macanally | 600/173 |
| 4,856,495 | 8/1989 | Tohjoh et al. . | |
| 4,860,732 | 8/1989 | Hasegawa et al. . | |
| 4,873,572 | 10/1989 | Miyazaki | 600/111 |
| 4,941,457 | 7/1990 | Hasegawa | 600/175 |
| 4,967,269 | 10/1990 | Sasagawa | 600/180 |
| 5,051,824 | 9/1991 | Nishigaki | 600/172 |
| 5,122,650 | 6/1992 | McKinley . | |
| 5,379,756 | 1/1995 | Pileski et al. . | |
| 5,402,769 | 4/1995 | Tsuji | 600/109 |
| 5,547,457 | 8/1996 | Tsuyuki et al. . | |
| 5,603,687 | 2/1997 | Hori et al. . | |
| 5,711,756 | 1/1998 | Chikama | 600/172 |
| 5,743,846 | 4/1998 | Takahashi | 600/166 |
| 5,800,341 | 9/1998 | McKenna | 600/173 |

Primary Examiner—John P. Leubecker
Attorney, Agent, or Firm—Armstrong, Westerman, Hattori, McLeland & Naughton

[57] ABSTRACT

An endoscope apparatus comprises an endoscope with a built-in solid state imaging device at a distal end portion of an insertion tube and a distal end optical adapter detachably connected to the distal end portion of the insertion tube of the endoscope. At least one objective optical system is provided in said distal end optical adapter and an optical image formed on said solid state imaging device through the distal end optical adapter is displayed on a TV monitor through a control device.

11 Claims, 9 Drawing Sheets

ENDOSCOPE APPARATUS

This is a divisional application of prior application Ser. No. 08/515,578, Aug. 16, 1995.

BACKGROUND OF THE INVENTION

1. Field of the Invention

The present invention relates to an endoscope apparatus having a distal end optical adapter connected to an endoscope with a built-in solid state imaging device.

2. Related Art Statement

In recent years, endoscopes which are capable of observing internal organs in the body cavity and performing several kinds of treatment using treatment tools inserted into treatment tool channels as the need arises by inserting an elongated insertion tube into the body cavity have been extensively used. These endoscopes are used not only in medical treatment but also applied to industrial use for observing and inspecting tubes in boilers, machines and chemical plant, or an internal engine.

In the endoscopes which are used as mentioned above, an electronic endoscope is included. In the electronic endoscope, a solid state imaging device, such as a charge coupled device (written as CCD in the following) is disposed at the distal end of an insertion tube, and an endoscope image formed on the imaging device is displayed on a monitor screen for observation.

Some of the electronic endoscopes for medical use are stereoscopic endoscopes which form an image acquired by each of two objective optical systems on a CCD built in an endoscope insertion tube so as to be capable of observing the image stereoscopically. The stereoscopic endoscopes are indicated in Japanese Patent Application Laid Open No. 64-26813/1989 and U.S. Pat, No. 5,122,650.

Further, in Japanese Patent Application Laid Open No. H1-197716/1989, two objective optical systems having different magnification are disposed and an image obtained by each objective optical system is formed on a CCD corresponding to each optical system, so that an endoscope for, what is called as telephotographic/wide which can observe two images including an ordinary observation image and a magnified image is shown.

On the other hand, in an electronic endoscope for industrial use, a distal end optical adapter type has been known in the art. In the distal end optical adapter, various kinds of objective optical systems for various uses have been arranged.

Further, in endoscopes used in the industrial field, some endoscope has a zooming function provided in an objective optical system and a function being capable of manually switching between a direct sight and a side sight, what is called as a pan viewing function has been highly required.

When a mechanism for performing a pan viewing function is provided at the distal end of the endoscope for industrial use, not only the endoscope distal end diameter becomes thick but also the structure is complicated. That has become a factor of increasing expenses.

The endoscopes which can perform stereoscopic vision observation shown in Patent Application Laid Open No. 64-26813/1989 and U.S. Pat. No. 5,122,650, and the endoscopes which can perform telephotographic/wide operation shown in Japanese Patent Application Laid Open No. H1-197716/1989 are exclusively used for stereoscopic vision observation or telephotographic/wide operation.

In addition, because the endoscopes form images acquired by two objective optical systems ordinarily use a pair of optical systems for stereoscopic vision observation, the two optical systems have the same f-number (brightness/stop value) and send the common illumination light to both optical systems. In other words, it was not necessary to adjust the quantity of illumination light for each optical system from a light source through a light guide. However, as mentioned above, if an observation image obtained by each objective optical system is formed on the CCD corresponding to each objective optical system and the common quantity of light illuminates two objective optical systems having different magnification in an endoscope performing telephotographic/wide operation by using the common quantity of light, an image having proper brightness for each optical system cannot be obtained, so that it was necessary to adjust and supply the quantity of illumination light being appropriate for each optical system.

OBJECT AND SUMMARY OF THE INVENTION

An object of the present invention is to provide an endoscope apparatus in which stereoscopic vision observation or two kinds of image observation, such as telephotographic/wide observation or a function including pan viewing is easily formed in addition to ordinary observation in an endoscope having a solid state imaging device.

Another object of the present invention is to provide an endoscope apparatus in which observation can be carried out in appropriate brightness when an image is observed using a function of stereoscopic vision or two kinds of telephotographic/wide images or pan viewing in an endoscope having a solid state imaging device.

In short, the endoscope apparatus of this invention comprises an endoscope with a built-in solid state imaging device at the distal end of the insertion tube, and a distal end optical adapter detachably connected to a distal end portion of the insertion tube of the endoscope, wherein at least one objective optical system is provided in the distal end optical adapter and an optical image formed on a solid state imaging device through the distal end optical adapter is displayed on a TV monitor through a control device.

The other characteristics and advantages of this invention will be sufficiently apparent in the following explanation.

BRIEF DESCRIPTION OF THE DRAWINGS

FIGS. 1 to 9 relate to a first embodiment of the present invention;

DETAILED DESCRIPTION OF THE PREFERRED EMBODIMENTS

Referring to FIGS. 1 to 9, a first embodiment of the present invention will be explained.

Figure 1:
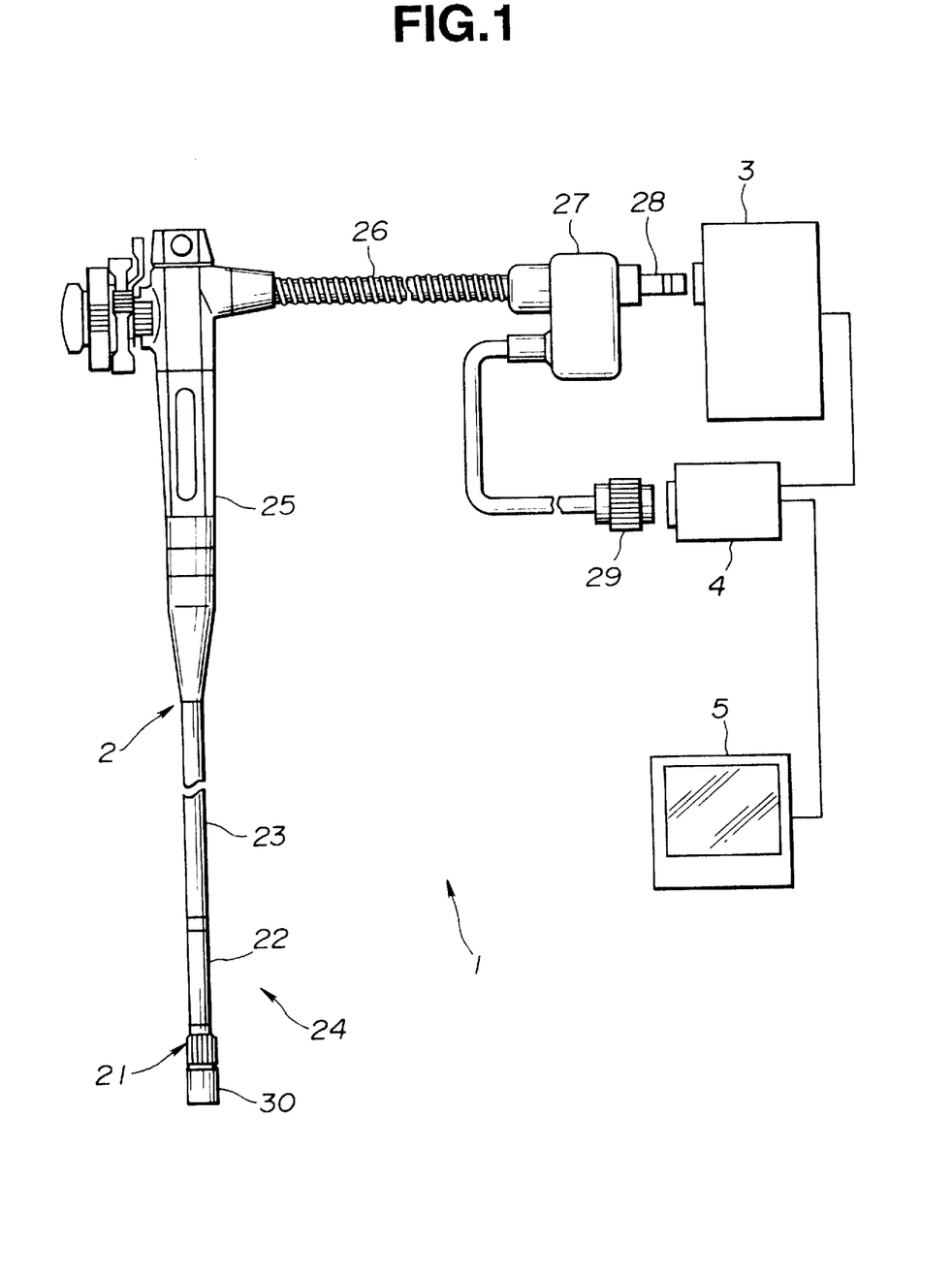
FIG. 1 is an illustration showing a conceptual construction of an endoscope apparatus.

As shown in FIG. 1, an endoscope apparatus 1 is formed of an endoscope 2, a light source 3 supplying illumination light to a light guide cable (not shown) built in the endoscope 2 a control device 4 driving and controlling a charge coupled device (CCD in the following) (stated later) built in the endoscope 2 and converting an electric signal of an optical image formed on a CCD and photoelectrically converted into a picture signal, and a TV monitor 5 displaying the picture signal of the optical image converted by the control device 4.

The endoscope 2 is formed of a distal end portion 21 to which a distal end optical adapter 30 stated later can be detachably connected and containing a built-in CCD, an insertion tube 24 consisting of an elongated and flexible bend portion 22 and soft portion 23, an operation portion 25 positioned on the proximal end of the insertion tube 24 and held by an operator, a universal cord 26, which is extended from the operation portion 25, containing a built-in light guide cable and signal cable, and a connector 27 provided at the end of the universal cord 26.

In the connector 27, a light guide connector 28 connected to the light source 3 is provided. Through the light guide connector 28, illumination light is transferred to the distal end portion of the endoscope insertion tube 24. Also, in the connector 27, an EL connector 29 having an electric contact for being connected to the control device 4 is provided. An electric signal of the optical image photoelectrically converted by a CCD disposed at the distal end portion 21 of the endoscope insertion tube 24 is led to the control device 4 through a signal cable.

Further, the light source 3, the control device 4, and the TV monitor 5 which are connected to the endoscope 2 are not separated as shown in FIG. 1 and can be formed as a unit as the occasion demands.

The configuration of the distal end optical adapter which is detachable with regard to the endoscope distal end portion 21 will be explained in reference to the drawings.

Figure 2:
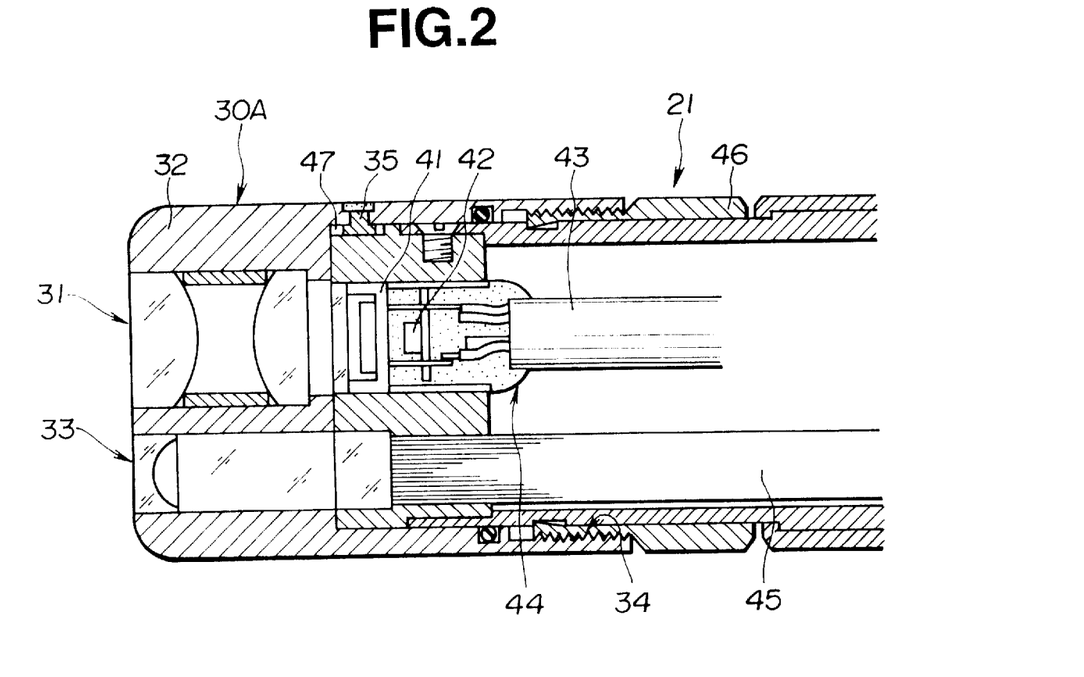
FIG. 2 is a sectional view of a configuration of an distal end optical adapter formed of an objective optical system.
Figure 3:
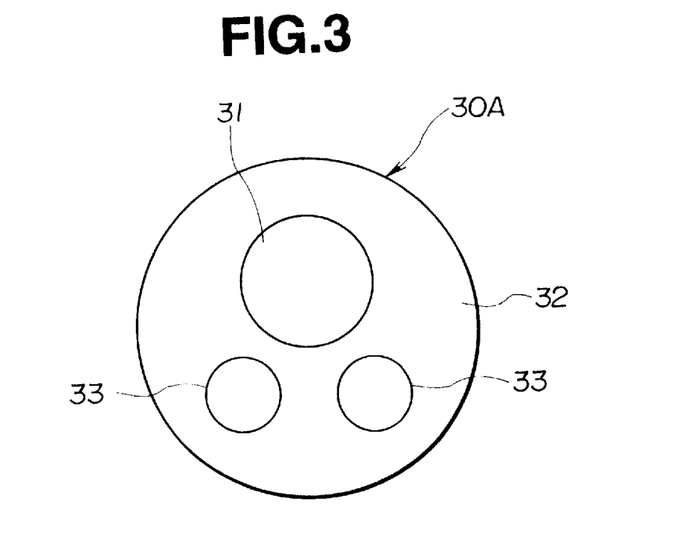
FIG. 3 is a front view of the distal end optical adapter in FIG. 2.

FIGS. 2 and 3 are examples of a distal end optical adapter 30A which is detachable with regard to the endoscope distal end portion 21. In the endoscope distal end portion 21, an image pickup unit 44 in which electric components including a CCD 41 and an IC 42 and a signal cable 43 are sealed from a CCD back surface to a cable connecting portion as a unit with adhesive to be molded and a light guide 45 are arranged. The light guide 45 is branched into two portions at the distal end of the endoscope distal end portion and follows two illumination optical systems 33 and 33 provided in the distal end optical adapter 30A as shown in FIG. 3. On the outer peripheral surface of the endoscope distal end portion 21, a screw for attaching and detaching an adapter 46 is fixed. Reference numeral 47 is a locational groove locating the optical system of the distal end optical adapter 30 so that the optical system of the distal end optical adapter 30 faces the optical system of the endoscope 2.

A distal end optical adapter 30A shown in FIGS. 2 and 3 used for ordinary observation has an objective optical system 31 in such a way that an optical image is formed on the CCD 41 built in the endoscope distal end portion 21. While the objective optical systems 31 and two illumination optical systems 33 and 33 are provided in a rigid portion 32 of the distal end optical adapter 30A, a screw portion 34 is formed on the proximal end inner peripheral surface of the rigid portion 32 as connecting means for being detachably connected to the endoscope distal end portion 21. Also, reference numeral 35 is a locational pin disposed in the locational groove 47.

The distal end optical adapter 30A and the endoscope distal end portion 21 are connected as a unit by spirally fitting the screw for attaching and detaching an adapter 46 provided on the outer peripheral surface of the endoscope distal end 21 and the screw portion 34 formed on the inner peripheral surface of the distal end optical adapter 30A. At this time, by disposing the locational pin 35 in the locational groove 47, the center of the optical axis of the CCD 41 coincides with the center of the optical axis of an objective optical system 31, so that an ordinary endoscope image is obtained and the endoscope 2 performing endoscope observation is formed.

Figure 4:
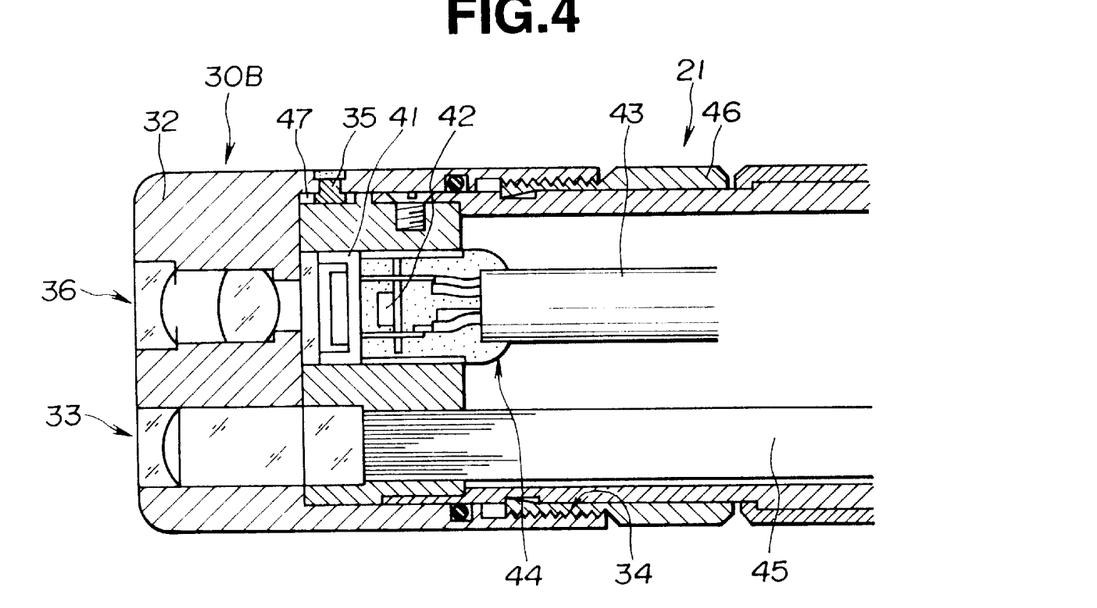
FIG. 4 is a sectional view of a configuration of a distal end optical adapter formed of two objective optical systems and an endoscope distal end portion.
Figure 5:
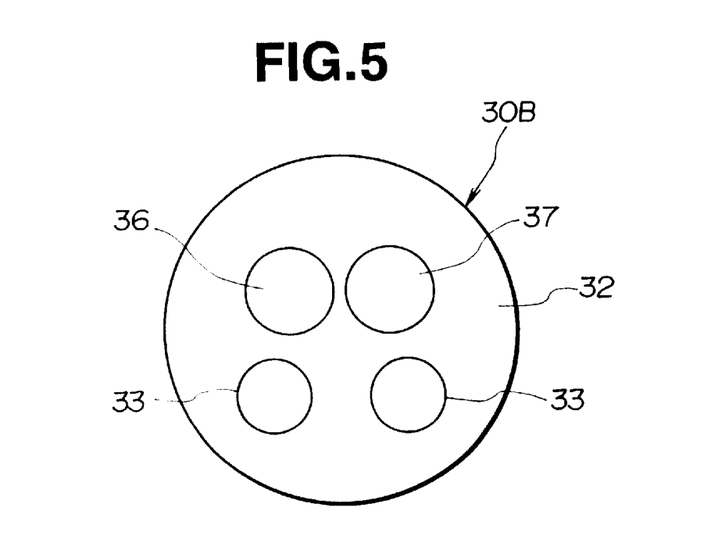
FIG. 5 is a front view of the distal end optical adapter in FIG. 4.

Referring to FIGS. 4 and 5, the distal end optical adapter 30 being detachable with regard to the endoscope distal end portion 21.

A distal end optical adapter 30B shown in the drawings is provided with two objective optical systems 36 and 37 in order to form two optical images on the CCD 41 built in the endoscope distal end portion 21. In the rigid portion 32 of the distal end optical adapter 30B, the objective optical systems 36 and 37 and the two illumination optical systems 33 and 33 are disposed.

The objective optical systems 36 and 37 can be two objective optical systems having the same function or different functions.

First, the two objective optical systems 36 and 37 having different functions will be explained.

The objective optical systems 36 and 37 provided in the distal end optical adapter 30B shown in the drawings are, for example, different in depth of observation and brightness. That is to say, the objective optical system 36 is formed to focus a near point and to stop down the diaphragm, and the objective optical system 37 is formed to focus a far point and to open the diaphragm. Therefore, by means of connecting the distal end optical adapter 30B to the endoscope distal end portion 21, a near point of a subject can be observed using the objective optical system 36 and a far point of a subject can be observed using the objective optical system 37. The endoscope being capable of observing a near point to a far point can be formed by connecting the distal end optical adapter 30B. The distal end optical adapter 30B is not limited to the one having different depth of observation and brightness and, for example, can be the one having different angles of view. In this case, the angle of view of the objective optical system 36 is specified to a narrow telephotographic angle in which, for example, 30° is set and the angle of view of the objective optical system 37 is specified to a wide angle in which, for example, 120° is set. The other configurations are the same as the configurations of the distal end optical adapter in the first embodiment. The same reference numbers are given to the same members and the explanation is omitted.

Accordingly, when observation is performed in the endoscope in which the distal end optical adapter 30B is connected to the endoscope distal end portion 21, first of all, a part we want to magnify in detail and observe can be observed in telephotographic/wide ways as using a zoom lens in the objective optical system 36 after an image in a wide range picked up by the objective optical system 37. At this time, by making illumination lenses disposed in the illumination optical systems 33 and 33 correspond to respective objective optical systems 36 and 37 to form the illumination lenses for a narrow angle and a wide angle, so that more effective observation can be conducted using the objective optical systems 38 and 37. Further, the objective optical system 36 for the narrow angle can be used for observing a turbine and the objective optical system 37 for the wide angle can be used for observing a pipe.

Figure 6:
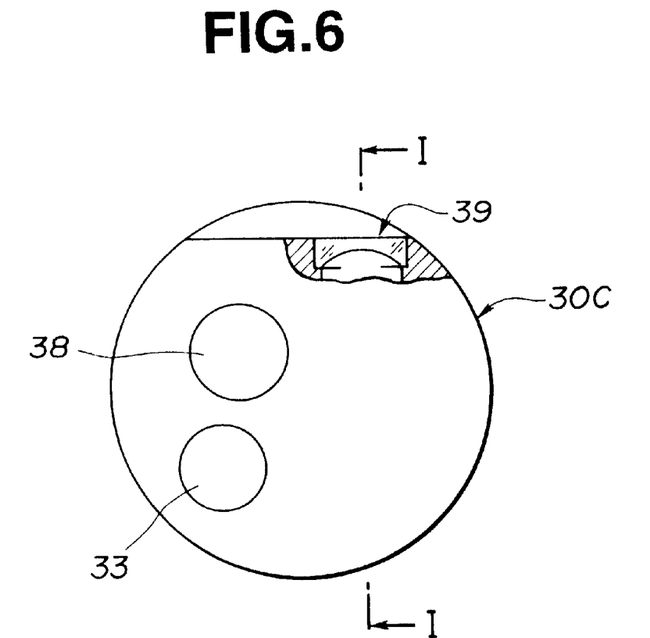
FIG. 6 is a sectional view showing another configuration of a distal end optical adapter formed of two objective optical systems.
Figure 7:
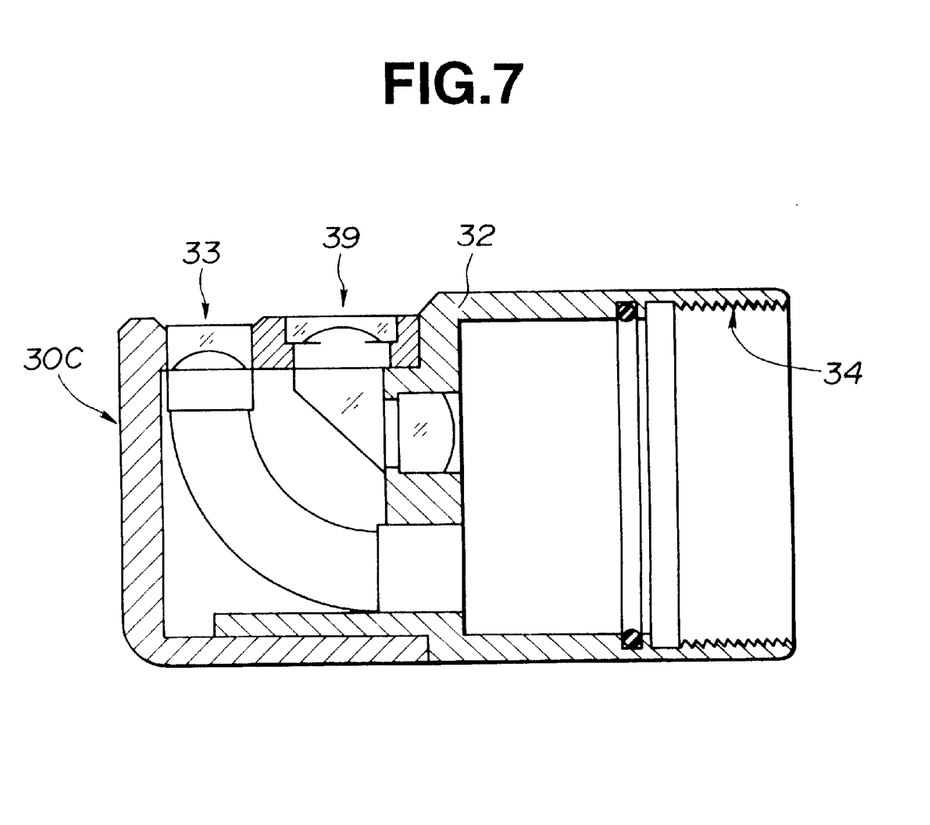
FIG. 7 is a sectional view of I—I in FIG. 6.

As shown in FIGS. 6 and 7, a distal end optical adapter 30C can be formed by combining a visual field direction of an objective optical system and an illumination optical system with a visual field direction of the other objective optical system and the other illumination optical system in different ways.

As shown in the drawings, the distal end optical adapter 30C is a direct sight type in which an observation plane of an objective optical system 38 faces the direction of an insertion tube of an endoscope and is a side sight type in which the other observation plane of an objective optical system 39 faces the perpendicular direction to the axis of the endoscope. In accordance with the specification of the objective optical systems 38 and 39, an endoscope which can observe both directions of a direct sight type and a side sight type can be formed. The other configurations are the same as the configurations of the aforesaid distal end optical adapter 30B. The same reference numerals are given to the same members and the explanation is omitted.

By connecting the distal end optical adapter 30C to the endoscope distal end portion 21, a subject positioned on the front surface of the endoscope distal end portion is observed by using the direct sight type objective optical system 38 and a subject positioned on the side surface of the endoscope distal end portion is observed by using the side sight type objective optical system 39, so that a subject can be observed as if a pan viewing function of the both directions of the direct sight and side sight is provided.

Figure 8:
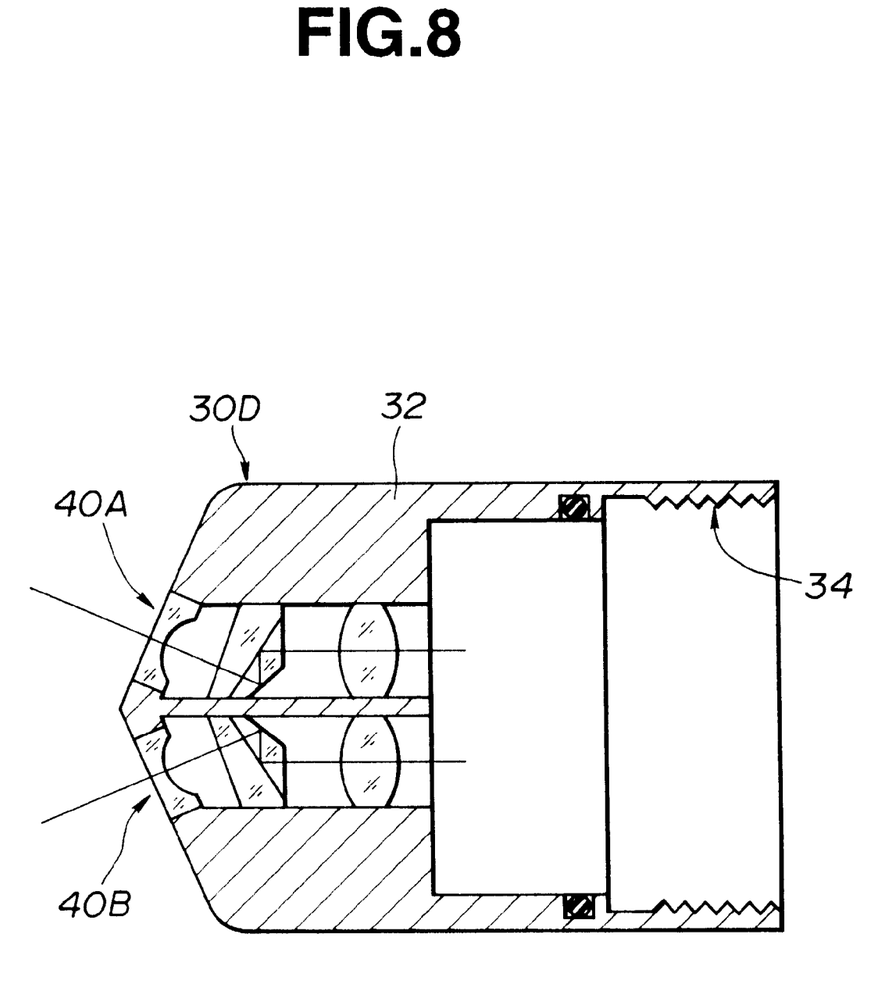
FIG. 8 is a sectional view of another configuration of a distal end optical adapter formed of two objective optical systems.

Additionally, a distal end optical adapter 30D shown in FIG. 8 forms an inclined sight type in which objective optical systems 40A and 40B face different directions. In this case, two illumination optical systems 33 and 33 are provided in the objective optical systems 40A and 40B, respectively, for illuminating each direction corresponding to the objective optical systems 40A and 40B. The other configurations are the same as the configurations of the aforesaid distal end optical adapter shown in the first embodiment. The same reference numerals are given to the same members and the explanation is omitted.

By connecting the distal end optical adapter 30D to the endoscope distal end portion 21, an endoscope which can observe a subject by using the two objective optical systems 40A and 40B facing different inclined directions with regard to the endoscope distal end portion and obtaining an extensive range of images is formed. Needless to say, it can be formed not only to make both objective optical systems inclined sight types but also to make only an objective optical system an inclined sight type and to make the other a direct or a side sight type.

Further, as explained above, when the plurality of objective optical systems including the distal end optical adapter 30B formed by combining objective optical systems having different depth of observation and brightness, the distal end optical adapter 30C formed by combining objective optical systems having different directions of visual fields, and the distal end objective optical adapter formed by combining objective optical systems having different angles of view are provided and an optical image is formed on a CCD through the plurality of objective optical systems, an observed image of appropriate brightness cannot be obtained because, if the same quantity of illumination light is emanated from a light guide arranged so as to correspond to each objective optical system by making the endoscope distal end portion branch at the distal end, there is difference in f-numbers of the objective optical systems between an observed image acquired by an objective optical system and an observed image acquired by the other objective optical system. Thus, it is necessary to cause the brightness of each observed image acquired by a plurality of optical images formed on a CCD through a plurality of objective optical systems to be appropriate brightness.

Figure 9:
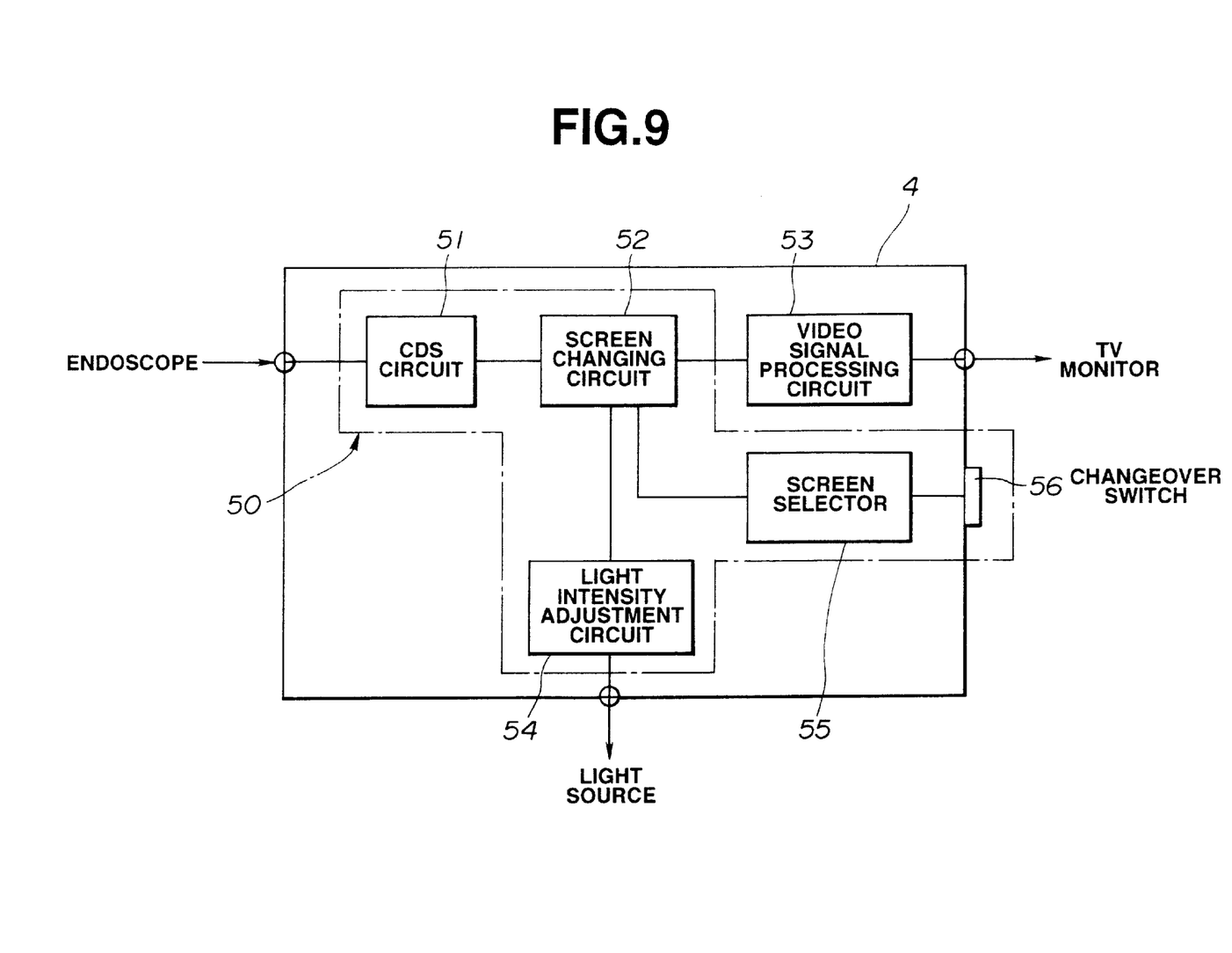
FIG. 9 is a block diagram of an example of a configuration of a control device.

Then, as shown in FIG. 9, a CDS circuit 51 for picking out a signal being the basis of a video signal, a screen changing circuit 52 for changing an image pickup surface of the CCD 41 to a right half, a left half or an ordinary whole screen, a video signal processing circuit 53 for generating a reference TV signal, a light intensively adjusting circuit 54 for supplying a control signal controlling the quantity of illumination light fed to the light guide connector 28 from the light source 3 to obtain an observed image of appropriate brightness and a screen selector 55 for controlling the screen changing circuit 52 are disposed and the control device 4 is formed by connecting a changeover switch 56 provided on a panel surface of the control device 4 to a screen selector 55. A light quantity control system 50 for obtaining two observed images having proper brightness by using a CCD is formed of the CDS circuit 51 of the control device 4, the screen changing circuit 52, the light intensity adjusting circuit 54, the screen selector 55 and a changeover switch 56.

In other words, when the brightness of one of the observed images obtained by two optical images formed on a CCD is inappropriate, an image formed on a right or left half of the image pickup surface of the CCD 41 is selected by operating the changeover switch 56. Then, a pixel number in the horizontal direction of the CCD 41 is counted in the screen selector 55 based on a control signal selected by the changeover switch 56. A signal for displaying only a right or left half of the image pickup surface is sent to the screen changing circuit 52. Then, in the screen changing circuit 52, a final screen changeover operation is performed.

After that, an electric signal in which an optical image formed of the image pickup surface of the CCD 41 selected by means of the screen changing circuit 52 is photoelectrically converted, and sent to the light intensity adjusting circuit 54. In the light intensity adjusting circuit 54, in order to adjust the quantity of the illumination light emanated from the light source 3 based on luminance information of an electric signal of the optical image transmitted from the image pickup surface of the selected CCD 41, for example, a control signal for driving a diaphragm blade (not shown) provided in the light source 3 is generated. Further, the diaphragm blade is adjusted by outputting the control signal generated by the light intensity adjusting circuit 54. Thus, proper quantity of illumination light is supplied to the illumination optical system corresponding to each objective optical system arranged in the distal end optical adapter from the light source 3 through the endoscope 2.

In this way, the quantity of illumination light emanated from the illumination optical system of the distal end optical adapter toward an object is properly adjusted to the brightness in accordance with each objective optical system, so that two observed images having proper brightness can be acquired using a CCD.

Next, the two objective optical systems having the same function will be explained.

Figure 10:
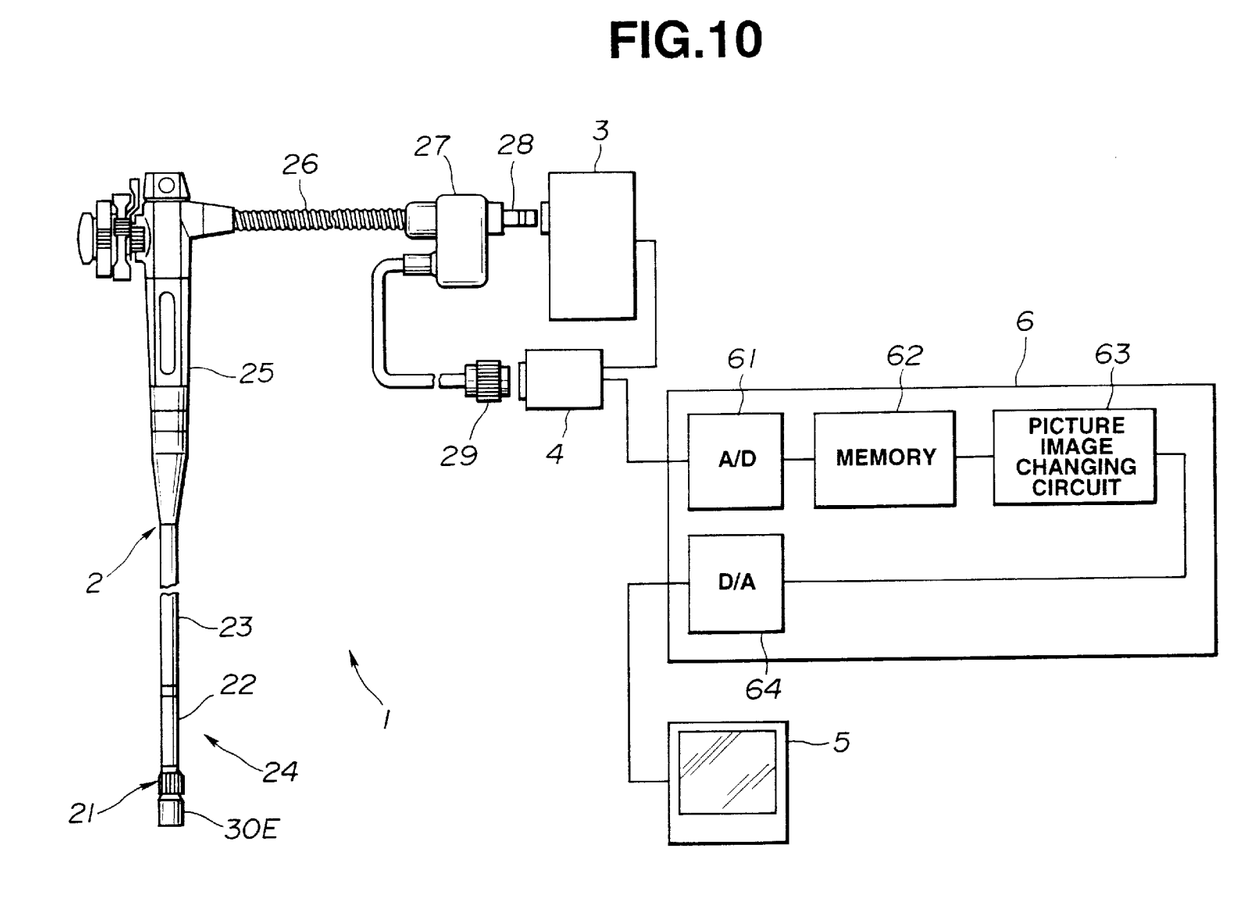
FIG. 10 is a conceptual construction of an endoscope apparatus in which another configuration of a distal end adapter is connected to an endoscope distal end.

In the case of a distal end optical adapter 30E in which the two objective optical systems 36 and 37 disposed in approximately the distal end optical adapter having similar configuration shown in FIG. 4 have the same function, a screen changing device 6 is provided in the endoscope apparatus 1 supplied with the endoscope 2 to which the distal end optical adapter 30E is connected as shown in FIG. 10.

Therefore, by connecting the distal end optical adapter 30E to an endoscope distal end portion 21, a video signal of a subject imaged in a different position in a CCD is transmitted to a picture image changing device 6 through the objective optical systems 36 and 37. Then, an endoscope which is capable of obtaining a stereoscopic image of an examined part is acquired by displaying the video signal of a subject taken by the objective optical systems 36 and 37 is displayed on the TV monitor 5 alternately through an A/D converter 61, a memory 62, a picture image changing circuit 63, and a D/A converter 64.

In this manner, endoscope apparatuses dealing with ordinary endoscope observation, telephotographic/wide observation, pan viewing observation and a stereoscopic vision observation can be easily constructed by making a detachable distal end optical adapter at the endoscope distal end portion consist of an objective optical system, an apparatus be capable of observing a near point to a far point by providing two objective optical systems, an apparatus be capable of performing telephotographic/wide observation using a wide-range picture image and a magnified image in detail, an apparatus be capable of observing both direct sight and side sight in such a way that a pan viewing function is provided, and further two functions of objective optical system be the same by exchanging adapters.

Also, in an endoscope with a built-in solid state imaging device, since an endoscope apparatus is formed of a control device and a picture changing device, simultaneous observation including stereoscopic vision observation and a direct sight/side sight observation and a simultaneous observation including wide/telephotographic observation can be inexpensively constructed in addition to ordinary observation without changing the formation of the aforesaid endoscope apparatus.

Also, the picture image changing device 6 is disposed between the control device 4 of the endoscope apparatus formed of the endoscope in which a distal end optical adapter with an objective optical systems disposed having different functions is connected to the endoscope distal end portion as mentioned above and the TV monitor 5, or is made to be the control device 4 having the screen changing circuit 52 shown in FIG. 9, the screen selector 55 and the changeover switch 56, so that not only stereoscopic vision observation can be easily performed but also only one of the picture images picked up by the objective optical system can be displayed or both pictures can be alternately displayed on the TV monitor 5. Additionally, pictures picked up by the objective optical system are switched and displayed by changing an exterior switch as the occasion demands, or an observation picture image can be more easily seen and an examination efficiency can be improved by selecting a desired one and displaying it at the center on the TV monitor 5. Further, instead of arranging a picture image changing device between the control device 4 and the TV monitor 5, needless to say, the control device 4 may have the function of the picture image changing device 6. When an image is formed on a CCD through two objective optical systems as stated above, in comparison with obtaining an image on a CCD, generation of flare is concerned. Therefore, it is desirable to coat CCD cover glass with coating for preventing flare. In addition, it is explained that a plurality of objective optical systems are two objective optical systems in the aforesaid embodiment; however, the number of objective optical systems can be three or more.

Next, a second embodiment of a light guide inserted into an endoscope will be explained by referring to FIG. 11.

As explained above, when an observation picture image is acquired by forming a plurality of optical images on a CCD by providing a plurality of objective optical systems including the distal end optical adapter 30B in which objective optical systems having different depth of observation and different brightness are combined, and the distal end optical adapter 30C in which objective optical systems having different directions of visual field are combined, a distal end optical adapter in which objective optical systems having different angles of view are combined, if the same quantity of illumination light is emanated from a light guide which is branched into two ends and disposed at the distal end of an endoscope distal end portion in accordance with each objective optical system, an observation picture image of appropriate brightness cannot be obtained because the difference is produced according to different f-number of each objective optical system between an observation picture image acquired by an objective optical system and an observation picture image acquired by another objective optical system.

For this reason, in this embodiment, an endoscope 70 is constructed as follows to make the brightness of each observation picture image obtained by a plurality of optical images formed on a CCD through a plurality of objective optical systems.

Figure 11:
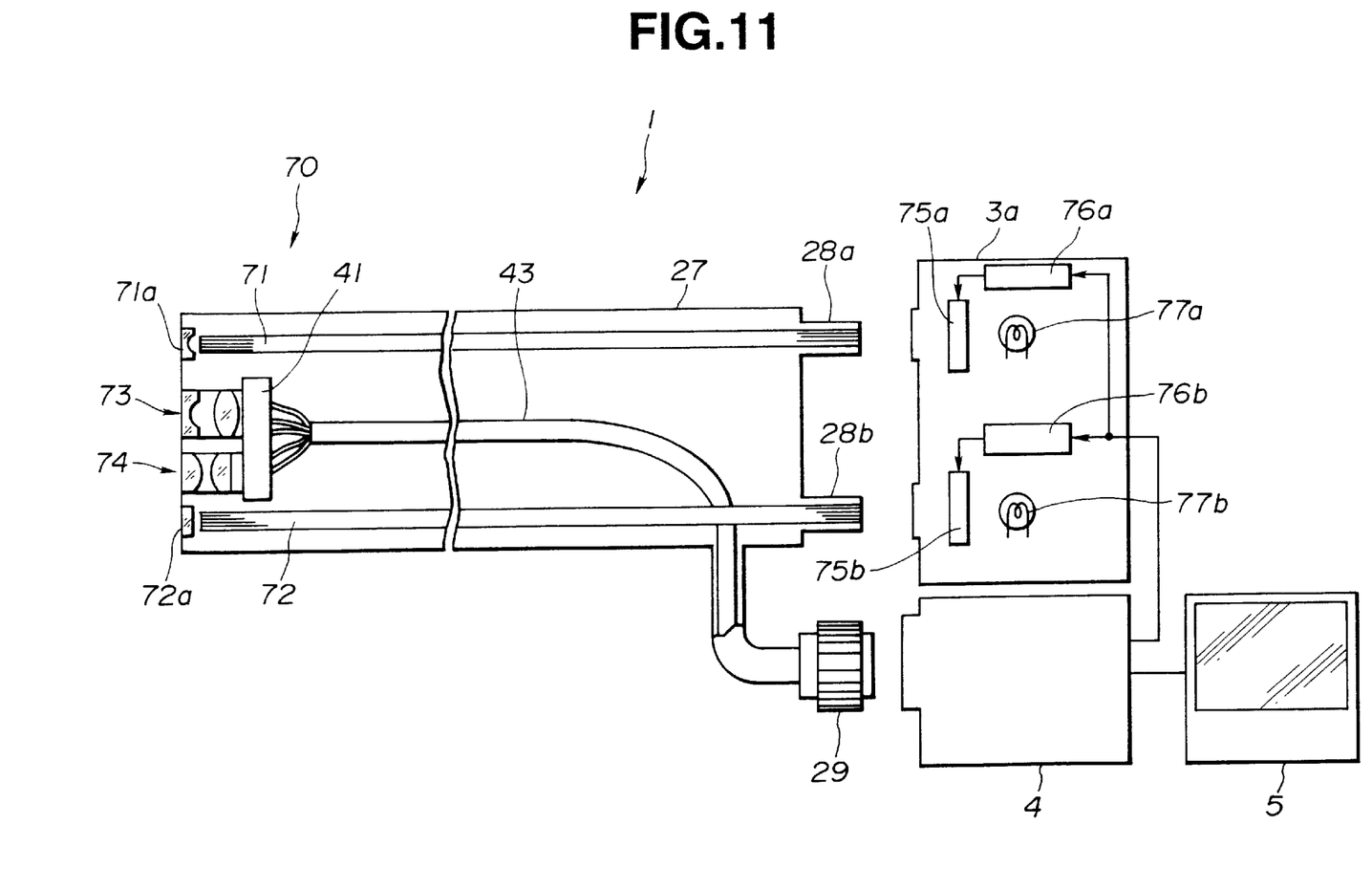
FIG. 11 is a sectional view explaining a second embodiment of an endoscope connectable to a distal end optical adapter.

As shown in FIG. 11, in the endoscope 70 of this embodiment, a first light guide 71 and a second light guide 72 are arranged in opposite positions to which, for example, two illumination optical systems are provided in the distal end optical adapter which can be detachably connected to the distal end portion of the endoscope 70, respectively.

That is to say, the first light guide 71 corresponding to a first objective optical system 73 facing the objective optical system 36 of the distal end optical adapter 30B shown in FIG. 4 and the second light guide 72 corresponding to a second objective optical system 74 facing the, objective optical system 37 of the distal end optical adapter 30B are provided. Reference numeral. 71a is a first illumination lens of the first light guide 71, and 72a is a second illumination lens of the second light guide 72. The other configuration of the endoscope 70 is the same as that of the endoscope 2. Thus, the same reference numerals are give to the same members and the explanation is omitted.

The first light guide 71 and the second light guide 72 are connected to a light source 3a through light guide connectors 28a and 28b provided on a connector 27a. In the light source 3a, while a first diaphragm device 75a for supplying illumination light to the first light guide 71, a first diaphragm driving portion 76a, and a first lamp 77a are provided, a second diaphragm device 75b for supplying illumination light to the second light guide 72, a second diaphragm driving portion 76b, and a second lamp 77b are provided.

When an endoscope apparatus 1 provided with the endoscope 70 constructed as mentioned above and the light source 3a observes an object, the object illuminated by the illumination light transmitted in the first light guide 71 and emanated from the illumination optical system of the distal end optical adapter forms an optical image on, for example, a right half of a CCD 41. The electric signal of an optical image photoelectrically converted by the CCD 41 and is transmitted to a control device 4. Similarly the object illuminated by the illumination light transmitted in the second light guide 72 and emanated from the illumination optical system of the distal end optical adapter forms an optical image on, for example, a left half of the CCD 41. The electric signal of the optical image photoelectrically converted in the CCD 41 is transmitted to the control device 4.

In a control device 4 to which the electric signal of these optical images are transmitted, a control signal for driving a first diaphragm driving portion 76a for controlling the first diaphragm device 75a for adjusting the quantity of illumination light emanated from the light source 3a to the object or the second diaphragm driving portion 76b for controlling the second diaphragm device 75b is produced.

Then, a control signal for driving the first diaphragm driving portion 76a or the second diaphragm driving portion 76b and being produced in the control device 4 is fed to the light source 3a to properly adjust, for example, a diaphragm blade which forms the first diaphragm device 75a or the second diaphragm device 75b equipped in the light source, so that appropriate brightness of each of a plurality of observation picture images obtained by means of a CCD are adjusted.

In this way, light guides are disposed by making the light guides correspond to a plurality of objective optical systems arranged in an endoscope. The quantity of illumination light emanated toward an object through a light guide and illumination optical systems can be appropriately adjusted by making the quantity of illumination light correspond to the brightness of the observation picture image based on an electric signal obtained from an optical image formed through each objective optical system. Accordingly, it is possible to cause the brightness of a plurality of observation picture images formed on a CCD to make the brightness of a plurality of observation images formed on a CCD coincide with appropriate brightness and observe the picture images.

Figure 12:
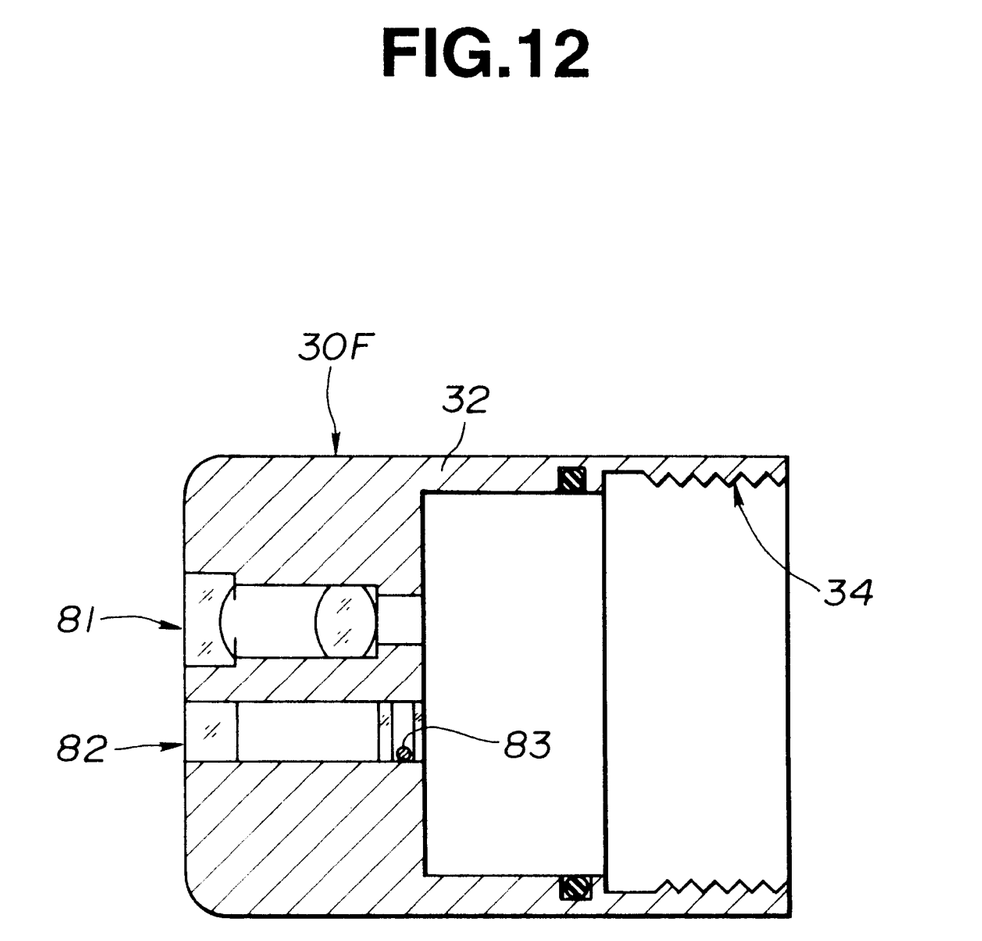
FIG. 12 is a sectional view showing a configuration of a distal end optical adapter in which gravity direction detecting means is disposed.

In the meantime, there is an observation optical system of an endoscope in which a steel bail for direction showing a gravity direction of an observation picture image. When observation was performed using the endoscope, it was found that nonconformity in which observation was difficult to be conducted because images of the steel ball for direction were overlapped in an observation picture image. Therefore, as shown in FIG. 12, a minute steel ball for direction 83 is disposed in an objective optical system 82 from the two objective optical systems 81 and 82 as gravity direction detecting means for detecting the gravity direction. Accordingly, because an observation picture image is obtained in the objective optical system 81 and the gravity direction of the objective optical system 82 can be found, an observation picture image can be easily seen.

It is not necessary that the objective optical system 82 containing a steel ball for direction indicating the gravity direction has forming image performance especially. The objective optical system can be sandwiched between transparent parallel planes. Additionally, an observation picture image easily observed can be obtained by making a picture for the gravity direction smaller than a picture for observation.

In this invention, it is apparent that working modes different in a wide range can be formed on the basis of this invention without departing from the spirit and scope of this invention. The invention is not restricted by its specific working modes except as limited by the appended claims.

What is claimed is:

1. An endoscope apparatus comprising:
    an endoscope with a built-in solid state imaging device at a distal end portion of an insertion tube without an optical lens system adjacent to the solid state imaging device; and
    a distal end optical adapter detachably connected to the distal end portion of the insertion tube of said endoscope, the distal end optical adapter having a plurality of objective optical systems to form a plurality of optical images on the image-pickup surface of the solid state imaging device, wherein directions of visual fields of the plurality of objective optical systems provided in said distal end optical adapter are different with respect to each other.

2. An endoscope apparatus according to claim 1, wherein some of the plurality of objective optical systems provided in said distal end optical adapter are direct sight types facing an insertion direction and some of the plurality of objective optical systems are side sight types facing a perpendicular direction to the insertion direction.

3. An endoscope apparatus according to claim 1, wherein some of the plurality of objective optical systems provided in said distal end optical adapter are direct sight types facing an insertion direction and some of the plurality of objective optical systems are inclined sight types facing inclined directions to the insertion direction with respect to each other.

4. An endoscope apparatus according to claim 1, wherein the plurality of objective optical systems provided in said distal end optical adapter are inclined sight types facing inclined directions to the insertion direction with respect to each other.

5. An endoscope apparatus according to claim 1, wherein at least one of the plurality of objective optical systems of the distal end optical adapter includes gravity direction detecting means for detecting a gravity direction.

6. An endoscope apparatus comprising:
    an endoscope with a built-in solid state imaging device at a distal end portion of an insertion tube without an optical lens system adjacent to the solid state imaging device;
    a first distal end optical adapter and a second distal end optical adapter detachably connectable to the distal end portion of the insertion tube of said endoscope, the first distal end optical adapter having one objective optical system to form an optical image on an image pickup surface of the solid state imaging device, and the second distal end optical adapter having a plurality of objective optical systems to form a plurality of optical images on the image-pickup surface of the solid state imaging device; and
    a control device to control display of the optical images on a monitor, the control device having image selecting means for selecting one of the plurality of optical images.

7. An endoscope apparatus according to claim 6, wherein a quantity of illumination light emanated from a light source to light guides provided in said endoscope is adjusted based on luminance information of an electric signal in which the optical image selected by said image selecting means is photoelectrically converted.

8. An endoscope apparatus comprising:

an endoscope with a built-in solid state imaging device at a distal end portion of an insertion tube without an optical lens system adjacent to the solid state imaging device; and a first distal end optical adapter and a second distal end optical adapter detachably connectable to the distal end portion of the insertion tube of said endoscope, the first distal end optical adapter having one objective optical system to form an optical image on an image pickup surface of the solid state imaging device and an illumination optical system corresponding to the one objective optical system, and the second distal end optical adapter having a plurality of objective optical systems to form a plurality of optical images on the image-pickup surface of the solid state imaging device and a plurality of illumination optical systems respectively corresponding to the plurality of objective optical systems, wherein said endoscope includes a light guide to provide illumination light to each illumination optical system provided in said first and second distal end optical adapters.

9. An endoscope apparatus comprising:

an endoscope with a built-in solid state imaging device at a distal end portion of an insertion tube without an optical lens system adjacent to the solid state imaging device; and a distal end optical adapter detachably connected to the distal end portion of the insertion tube of said endoscope, the distal end optical adapter having a plurality of objective optical systems to form a plurality of optical images on the image-pickup surface of the solid state imaging device and a plurality of illumination optical systems respectively corresponding to the plurality of objective optical systems, wherein said endoscope includes a plurality of light guides to respectively provide illumination light to the corresponding illumination optical systems provided in said distal end optical adapter.

10. An endoscope apparatus according to claim 9, wherein a plurality of lamps corresponding to the plurality of light guides provided in the endoscope, respectively are provided in a light source.

11. An endoscope apparatus according to claim 10, wherein the plurality of lamps provided in said light source correspond to the light guides provided in said endoscope in a one to one ratio, and the quantity of illumination light supplied from each of said lamps to the corresponding light guide is independently controlled.

* * * * *